United States Patent [19]

Hallewell et al.

[11] Patent Number: 5,084,390
[45] Date of Patent: Jan. 28, 1992

[54] SUPEROXIDE DISMUTASE POLYMERS

[75] Inventors: Robert A. Hallewell, San Francisco; Guy Mullenbach, Oakland, both of Calif.

[73] Assignee: Chiron Corporation, Emeryville, Calif.

[21] Appl. No.: 488,363

[22] Filed: Feb. 14, 1990

Related U.S. Application Data

[63] Continuation of Ser. No. 26,143, Mar. 16, 1987, abandoned.

[51] Int. Cl.$^5$ .................. C12N 9/96; C12N 9/02; A61K 37/50
[52] U.S. Cl. ........................... 435/188; 435/189; 435/320.1; 435/256; 435/10; 435/14; 435/47; 424/94.4; 536/27
[58] Field of Search ............... 435/188, 189, 320, 255, 435/256, 942; 424/94.4; 536/27; 935/10, 14, 47

[56] References Cited

U.S. PATENT DOCUMENTS 3,654,083  4/1972  Moelker .............................. 195/63

FOREIGN PATENT DOCUMENTS 0180964   5/1986  European Pat. Off. .
0196056  10/1986  European Pat. Off. .
W001503   4/1983  PCT Int'l Appl. .

OTHER PUBLICATIONS

Jabusch et al., (1980) Biochemistry 19:2310-2316.
Petrone et al., (1980) Proc. Natl. Acad. Sci. 77:1159-1163.
Pyatak et al., (1980) Res. Commun. in Chem. Path. & Pharmacol. 29:113-127.
Boccu et al., (1982) Pharmacol. Res. Commun. 14:113-120.
Beauchamp et al., (1983) Anal. Biochem. 131:25-33.
Veronese et al., (1983) J. Pharm. & Pharmacol. 35:757-758.
Wong et al., (1980) Agents Actions 10:231-239.
Turrens et al., (1984) J. Clin. Invest. 73:87-95.
Freeman et al., (1985) Fed. Proc. 44:2591-2595.
Neuberger et al., (1984) Nature 312:604-608.

Primary Examiner—David M. Naff
Assistant Examiner—Charles L. Patterson, Jr.
Attorney, Agent, or Firm—Irell & Manella

[57] ABSTRACT

Recombinant Cu/Zn superoxide dismutase (SOD) polymers having an extended in vivo half-life composed of SOD monomers covalently coupled to each other, carboxy terminus to amino terminus, by a polypeptide spacer such as a fragment of the hinge region of an immunoglobulin.

20 Claims, 7 Drawing Sheets

CTGCAGCGTCTGGGGTTTCCGTTGCAGTCCTCGGAACCAGGACCTCGGCGTGGCCTAGC

```
              1                                            10
       Met Ala Thr Lys Ala Val Cys Val Leu Lys Gly Asp Gly
GAGTT  ATG GCG ACG AAG GCC GTG TGC GTG CTG AAG GGC GAC GGC

20
Pro Val Gln Gly Ile Ile Asn Phe Glu Gln Lys Glu Ser Asn Gly
CCA GTG CAG GGC ATC ATC AAT TTC GAG CAG AAG GAA AGT AAT GGA 30                                    40
Pro Val Lys Val Trp Gly Ser Ile Lys Gly Leu Thr Glu Gly Leu
CCA GTG AAG GTG TGG GGA AGC ATT AAA GGA CTG ACT GAA GGC CTG

50
His Gly Phe His Val His Glu Phe Gly Asp Asn Thr Ala Gly Cys
CAT GGA TTC CAT GTT CAT GAG TTT GGA GAT AAT ACA GCA GGC TGT 60                                    70
Thr Ser Ala Gly Pro His Phe Asn Pro Leu Ser Arg Lys His Gly
ACC AGT GCA GGT CCT CAC TTT AAT CCT CTA TCC AGA AAA CAC GGT

80
Gly Pro Lys Asp Glu Glu Arg His Val Gly Asp Leu Gly Asn Val
GGG CCA AAG GAT GAA GAG AGG CAT GTT GGA GAC TTG GGC AAT GTG 90                                    100
Thr Ala Asp Lys Asp Gly Val Ala Asp Val Ser Ile Glu Asp Ser
ACT GCT GAC AAA GAT GGT GTG GCC GAT GTG TCT ATT GAA GAT TCT

110
Val Ile Ser Leu Ser Gly Asp His Cys Ile Ile Gly Arg Thr Leu
GTG ATC TCA CTC TCA GGA GAC CAT TGC ATC ATT GGC CGC ACA CTG 120                                   130
Val Val His Glu Lys Ala Asp Asp Leu Gly Lys Gly Gly Asn Glu
GTG GTC CAT GAA AAA GCA GAT GAC TTG GGC AAA GGT GGA AAT GAA

140
Glu Ser Thr Lys Thr Gly Asn Ala Gly Ser Arg Leu Ala Cys Gly
GAA AGT ACA AAG ACA GGA AAC GCT GGA AGT CGT TTG GCT TGT GGT 150       153
Val Ile Gly Ile Ala Gln OC
GTA ATT GGG ATC GCC CAA TAA
```

FIG. 1

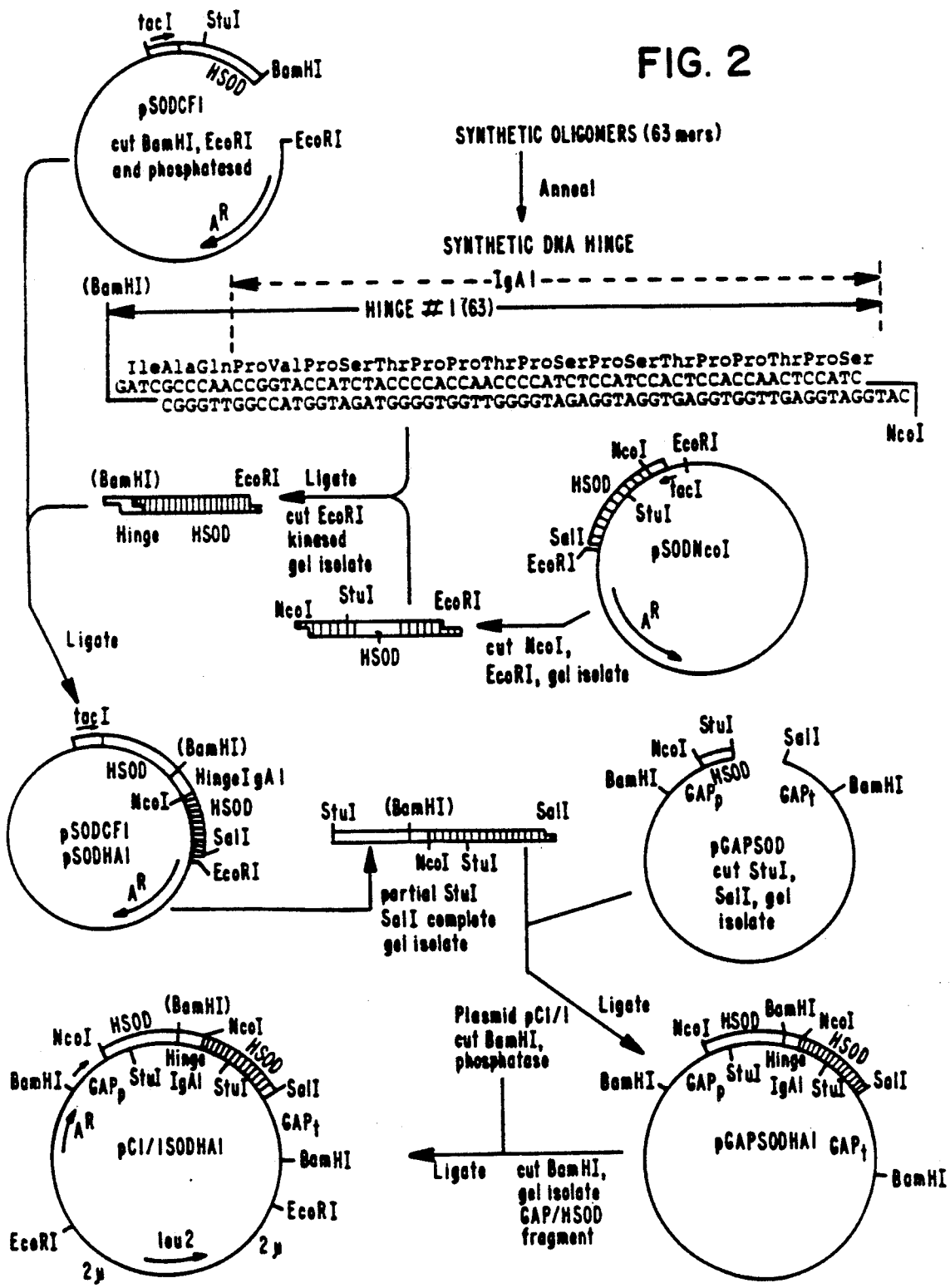

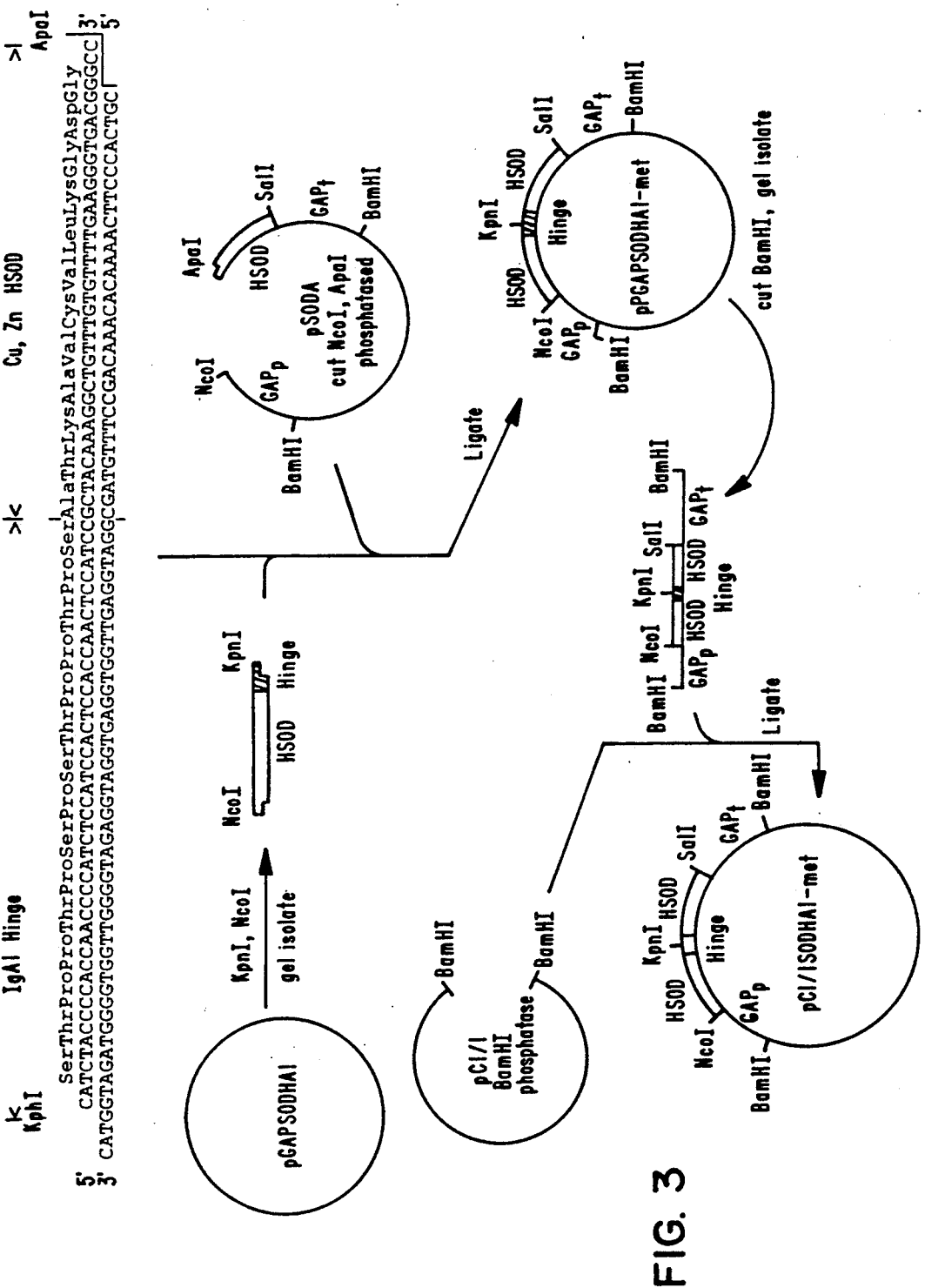

SUPEROXIDE DISMUTASE POLYMERS

This application is a continuation of application Ser. No. 026,143, filed Mar. 16, 1987, now abandoned.

TECHNICAL FIELD

This invention is in the fields of protein chemistry and genetic engineering. More particularly, it relates to polymers of Cu/Zn superoxide dismutase (hereinafter referred to as SOD) that exhibit longer half-lives in vivo than native SOD.

BACKGROUND

SOD is a member of a family of superoxide dismutases which, because of their ability to catalyze the destruction of superoxide ions, renders them useful in a variety of therapeutic settings such as in reducing perfusion injury and in treating inflammation. The amino acid sequence of human SOD (hSOD) is described in Jabusch et al, Biochemistry (1980) 19:2310-2316. The cloning and sequencing of hSOD cDNA and the production of hSOD in bacteria and yeast are described in EPA 84111416.8 (published Apr. 24, 1985 under number 0 138 111). hSOD is normally a homodimer of two chains bound together by hydrophobic interaction. The homodimer has a molecular weight of approximately 32 kd.

SOD is rapidly removed from circulation by the kidney. Rat studies indicate its half-life in serum is on the order of seven minutes. The limited circulatory life of injected SOD may severely limit clinical approaches to SOD pharmacology and the effectiveness of treatment. In order to eliminate SOD's susceptibility to removal by the kidney, prior workers have conjugated SOD with macromolecules such as Ficoll (PNAS, USA (1980) 77:1159-1163), polyethylene glycol (Res. Commun. in Chem. Path. & Pharmacol. (1980) 29:113-120; Pharmacol. Res. Commun. (1982) 14:113-119; Anal. Biochem. (1983) 131:25-30; and J. Pharm. & Pharmacol. (1983) 35:757-763), and human serum albumin (Agents Actions (1980) 10:231-240). SOD has been entrapped in liposomes for the same purpose (J. Clin. Invest. (1984) 73:87-95; Fed. Proc. (1985) 44:2591-2595).

An object of the present invention is to provide SOD in a novel polymeric form that has an extended circulatory life and retains the activity of SOD. This polymeric SOD may be made using recombinant DNA techniques. Its manufacture does not involve any chemical derivatization such as that described above. A preferred embodiment of this polymeric SOD comprises SOD monomers covalently linked to each other via a polypeptide that has an amino acid sequence, such as the sequence of the hinge region of immunoglobulin, which naturally acts as a means of coupling functional domains of biologically active proteins in a manner that allows them to fold and function independently. In this regard, *Staphylococcus aureus* nuclease and the c-myc oncogene have both been attached to a murine immunoglobulin heavy chain via the hinge region of the immunoglobulin to produce functional antibody-enzyme complexes (Nature (1984) 312:604-608).

DISCLOSURE OF THE INVENTION

The invention provides novel SOD polymers formed from SOD units of at least two SOD monomers covalently coupled carboxy terminus to amino terminus by a polypeptide spacer of at least three amino acids.

Parenteral pharmaceutical compositions containing these new SOD polymers and therapeutic methods that employ them are other aspects of the invention.

The SOD units are also novel and are a part of the invention.

The invention also encompasses the biological materials (DNA encoding the SOD polymers, expression vectors containing such DNA, and host microorganisms or cells capable of expressing such DNA) and the methods involved in making the SOD polymers.

BRIEF DESCRIPTION OF THE DRAWINGS

FIG. 1 shows the sequence of a DNA fragment that encodes hSOD monomer and the amino acid sequence of hSOD monomer.

FIG. 2 is a flow chart for the construction of the plasmid pCl/1SODHA1 described in the examples.

FIG. 3 is a flow chart for the construction of the plasmid pCl/1SODHA1-met described in the examples.

MODES FOR CARRYING OUT THE INVENTION

A. Definitions

Figure 4:
FIG. 4 is a photograph of an SDS gel analysis of the protein identified as SODHA1 in the examples, through its purification.

The term "SOD monomer" intends the monomer (single chain) that forms the normal SOD homodimer.

The term "SOD unit" intends a molecule composed of at least two SOD monomers covalently coupled head-to-tail by a polypeptide spacer.

The term "SOD multimer" intends a composition composed of at least two SOD units bound together by hydrophobic interaction.

The term "SOD" intends a polypeptide having the amino acid sequence of native Cu/Zn superoxide dismutase and analogs or muteins thereof having substantially homologous amino acid sequences thereto which may differ in one or more amino acid substitutions, additions or deletions but still retain the enzymatic activity of native Cu/Zn superoxide dismutase. Examples of such analogs are those described in commonly owned copending U.S. application Ser. No. 003578, filed Jan. 15, 1987. The term encompasses SOD of various mammalian species. hSOD is preferred for use in humans. The term "substantially homologous" intends at least about 90% identity, more usually at least about 95% identity, in amino acid sequence.

The number of SOD units in the polymers of the invention will usually be between about 2 and about 10. Preferably the number of units is between 2 and 4 and most preferably the number of units is 2. The polymers are generally linear with the monomers covalently coupled carboxy terminus to amino terminus via the polypeptide spacer. The spacer will normally be 3 to 1000 amino acids in length, preferably between about 10 and about 100 amino acids in length. Its amino acid composition and sequence is such that it is substantially nonimmunogenic (i.e., does not cause an unacceptable immune response), and substantially insensitive to proteases (i.e., is not readily digested by the proteases that occur in circulation). The spacer will typically be rich in proline and the proline content of the spacer will normally be in the range of 20 to 50 number percent, preferably 25 to 45 number percent. The sequence also preferably lacks cysteines (to avoid the likelihood of cross-linking) and is preferably substantially nonhydrophobic. The spacer's hydrophobicity may be determined by summing the hydrophobicities of the individual amino acids (measured by partition coefficient tests) of which it is composed. A substantially nonhydrophobic sequence will measure neutral or hydrophilic.

Preferred spacers have amino acid sequences that correspond to sequences, such as those of the hinge region of immunoglobulins, that act as connector domains that link functional domains of biologically active endogenous (naturally-occurring in the individual to whom the SOD polymer is to be administered) proteins in a manner that allows them to assume an appropriate tertiary structure and function independently.

A particularly preferred subgroup of SOD polymers are those represented by the formula:

(SOD monomer-IgA-SOD monomer)$_x$ where SOD monomer is as defined previously, IgA represents a 10 to 100 amino acid long segment of IgA hinge region, and x is an integer in the range of 2 and 4, inclusive. Preferably x is 2.

The SOD polymers of this invention are made by recombinant DNA techniques. Briefly, DNA encoding the SOD unit is made by ligating DNA fragments encoding the SOD monomer and spacer together. The DNA may be genomic, cDNA or synthetic DNA. The DNA encoding the polymer may be inserted into suitable prokaryotic or eukaryotic replicons (a genetic element such as a plasmid, a chromosome, or a virus that behaves as an autonomous unit of polynucleotide replication within a cell), the resulting expression vectors incorporated into suitable host organisms or cells, the recombinant organism or cell grown under conditions that result in expression of the DNA, and the resulting SOD polymer isolated from the host or, if secreted, from the growth medium using the same techniques as are described in EPA 841111416.8 to produce recombinant hSOD. The disclosure of that EPA is incorporated herein by reference.

In creating an expression vector, the DNA encoding the SOD unit is located in the vector with the appropriate control DNA sequences, which include a promoter, a ribosomal binding site, and transcriptional and translational stop codons. The positioning and orientation of the coding sequence with respect to the control sequence is such that the coding sequence is transcribed under the "control" of the control sequences—i.e., the promoter will control the transcription of the mRNA derived from the coding sequence, the ribosomes will bind at the ribosomal binding site to begin the translational process, and the stop codon used to terminate translation will be upstream from the transcriptional termination codon. In addition to control sequences, it may be desirable to add regulatory sequences which allow for regulation of the expression of the SOD polymer gene relative to the growth of the host cell.

The SOD polymers of the invention may be used for the same purposes as SOD. Because they have longer half-lives in circulation, the SOD polymers are particularly useful in pharmaceutical formulations intended for parenteral (intramuscular, intravenous, intraperitoneal, etc.) administration. The SOD polymers may be used in human or veterinary medicine to treat (i.e. cure, alleviate or prevent) a variety of conditions. They are useful as antiinflammatory agents, chemopreventive agents to prevent oncogenesis and tumor promotion, protective agents to reduce cytotoxic and cardiotoxic effects of anticancer drugs or protect ischemic tissue. Like native SOD, the SOD polymers catalyze the reduction of superoxide radicals to hydroperoxide and molecular oxygen and may thus be used to reduce perfusion injury following ischemia, prolong the viability of excised isolated organ transplants, reduce injury on reperfusion following organ transplant or spinal cord ischemia, reduce cardiac infarct size, reduce spinal cord injury and treat bronchial pulmonary dysplasia.

When used to treat tissues in vitro the polymer will be added to the perfusion or culture medium. When used in vivo, the SOD polymer may be administered neat or admixed in effective amounts with pharmaceutically acceptable injectable vehicles. Preferably the SOD polymer is conveniently stored lyophilized with sugar, usually sucrose, usually in a ratio of 1:2 w/w. The lyophilized SOD polymer is conveniently reconstituted in a suitable diluent for the particular application. For example, to treat inflammatory joint disease the SOD polymer may be reconstituted in physiologic saline in a volume convenient for intraarticular administration.

The dose of SOD polymer administered to an individual will depend upon the nature of the individual being treated, the mode of treatment and the condition being treated. In general the amount administered must be sufficient to provide an enzymatically effective amount of the SOD polymer at the desired site of treatment. In this regard when the SOD polymer is administered systemically, larger doses will typically be required than when the SOD polymer is administered locally at the site that requires treatment. By way of example, human patients having inflammatory joint disease are treated by a weekly intraarticular injection into a joint afflicted with the disease of a solution having hSOD mutein in a suitable diluent in an amount effective to reduce inflammation, usually 1 to 10 mg, more usually 2 to 6 mg. The injections are given weekly for a period of time sufficient to reduce inflammation, usually for 2 to 8 weeks, more usually for 4 to 6 weeks. Because the articular capsule limits leakage of the high molecular weight compound each afflicted joint should be treated with the required dosage. When used to minimize post-ischemic tissue damage the human patient is administered 10 mg to 1,000 mg, more usually 50 mg to 500 mg of SOD polymer in a suitable diluent during the ischemic reaction. When the patient suffers ischemia due to a disease the solution is administered intravenously or intraarterially as a bolus dosage or a continuous infusion. In such situations the SOD polymer may be administered in conjunction with fibrinolytic agents such as urokinase, streptokinase or tissue plasminogen activator (TPA). When ischemic damage is due to a surgical procedure, SOD polymer is administered during surgery. This application finds particular use in organ transplant surgery where SOD is preferably administered prior to reirrigation of the organ and is also useful in any other surgery where bloodflow to an organ is interrupted, such as open heart surgery.

The following examples further illustrate the invention. These examples are not intended to limit the invention in any manner.

Construction of Yeast Plasmid pCl/lSODHA1

The construction of plasmid pCl/lSODHA1 is depicted in FIG. 2.

DNA oligomers (63 mers) were synthesized and annealed to form a fragment encoding the human IgAl hinge region beginning at amino acid residue 226 to avoid the Cys 225 residue (see Kabat, E. A., et al., In Sequences of Proteins of Immunological Interest (1983) U.S. Dept. of Health & Human Resources, PHS, NIH, p. 179, for sequence of IgA heavy chain) with BamHI and NcoI sites at its ends. The fragment had the sequence shown below.

This vector fragment was ligated to the 327 bp hSOD fragment to produce plasmid pSODCFl.

pSODCFlSODHA1 was subjected to partial digestion with StuI and complete digestion with SalI, and a 560 bp StuI-SalI framgment was gel isolated from the digest.

The plasmid pGAPSOD was cut with StuI and SalI and vector DNA was gel purified. pGAPSOD is a yeast promoter vector containing the hSOD gene under the regulation of the glyceraldehyde-3-phosphate dehydrogenate (GAP) promoter and terminator. Details of its composition and construction are described in commonly owned U.S. patent application Ser. No. 609,412, filed May 11, 1984, the disclosure of which, as it relates to this plasmid, is incorporated herein by reference. (The plasmid is designated pPGAPSOD in Ser. No. 609,412.)

The 560 bp StuI-SalI fragment from pSODCFlSOD-

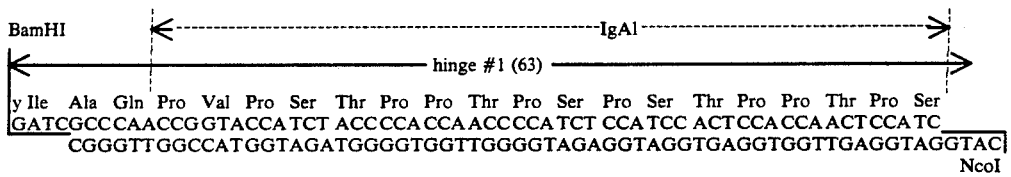

This fragment was used to make plasmid pSODCFl-SODHA1 encoding bacterial expression of spacer-linked hSOD monomers as follows.

The plasmid phSOD (designated pSODNcoI in FIG. 2 and described in commonly owned EPO 0138111, the disclosure of which, as it relates thereto, is incorporated herein by reference) was cut with NcoI and EcoRI and a NcoI-EcoRI fragment containing the hSOD DNA shown in FIG. 1 was gel isolated from the digest. This fragment was ligated to the synthetic DNA fragment encoding the IgA hinge region. The ligation product was kinased, cut with EcoRI and the BamHI-EcoRI fragment encoding the IgA hinge fused to hSOD was gel isolated.

The IgA hinge-hSOD fragment was then inserted into plasmid pSODCFl, which had been cut with BamHI and EcoRI and phosphatased to form plasmid pSODCFlSODHA1.

pSODCFl was derived from plasmid pSODX8 (described in Hallewell, et al, Nucleic Acids Res. (1985) 13:2017-2034) as follows. Plasmid pSODX8 was cut with StuI and SalI. An approximately 400 bp fragment was gel isolated and partially digested with Sau3A and a 327 bp hSOD fragment was recovered. Plasmid pSODX16 (described in Nucleic Acids Res. (1985) 13:2017-2034) was cut with StuI and BamHI and the large vector fragment was gel isolated from the digest.

HA1 was ligated with the vector DNA from pGAPSOD to form plasmid pGAPSODHA1. pGAPSODHA1 was then cut with BamHI and the resulting BamHI cassette (GAP/hSOD fragment) was gel isolated. The cassette was then subcloned in the expression orientation in the yeast shuttle vector pCl/1, which had been digested with BamHI. Plasmid pCl/1 is a derivative of pJDB219 (Beggs, Nature (1978) 275:104) in which the region corresponding to bacterial plasmid pMB9 in pJDB219 is replaced by pBR322.

Construction of Yeast Plasmid pCl/lSODHA1-met

The construction of pCl/lSODHA1-met is shown in FIG. 3. This plasmid was designed for expression of an hSOD polymer identical to the hSOD expressed by pCl/lSODHA1, except for the elimination of the methionine at the C-terminus of the IgA1 sequence of pCl/lSODHA1. In this regard, methionine is normally removed from the N-terminus of hSOD and it was felt the elimination of this met might lessen the likelihood of immunogenicity.

The DNA fragment shown below encoding portions of the IgA1 hinge and hSOD was synthesized.

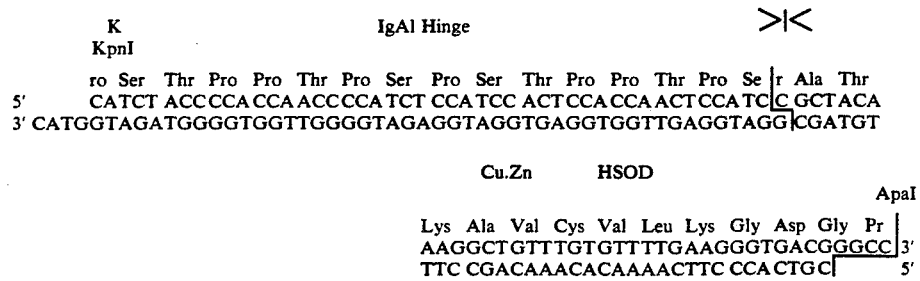

pGAPSODHA1 was cut with KpnI and NcoI and the small hSOD-IgA1 hinge fragment was gel purified from the digest.

The plasmid pSODA, a yeast promoter vector containing an hSOD gene in which the Cys6 codon is replaced with an Ala-encoding triplet described in commonly owned U.S. patent application Ser. No. 003578, filed Jan. 15, 1987, the disclosure of which is incorporated herein by reference to the extent it relates to said plasmid, was cut with NcoI and ApaI and phosphatased. (pSODA is designated pYSODA in Ser. No. 003578.) The resulting vector DNA was ligated with the above-described synthetic DNA fragment and the KpnI-NcoI fragment from pGAPSODHA1 to form plasmid pGAPSODHA1-met. A BamHI expression cassette was isolated from the plasmid by digestion with BamHI and gel purification and subcloned into pC1/1 as above to form the yeast expression vector pC1/1SODHA1-met.

Preparation of Recombinant Yeast Strains

Plasmids pC1/1SODHA1 and pC1/1SODHA1-met were transformed into *S. cerevisiae* strain PO17 (Mat a, leu 2-04, cir°), as described in PNAS USA (1978) 75:1929–1933, selecting on agar medium lacking leucine, to produce recombinant strains that produce an hSOD unit composed of two hSOD monomers joined covalently by the 23 amino acid IgA1 hinge fragment shown above (designated SODHA1) and a similar unit lacking a met residue at the N-terminus of the second hSOD unit (designated SODHA1-met).

Yeast strain PO17 was obtained by isolating a spontaneous revertant strain 2150-2-3 (Mat a, ade 1, leu 2-04, cir°). To isolate the revertant PO17, 2150-2-3 yeast cells were grown in YEPD, washed in medium without adenine and about $6 \times 10^8$ cells were plated onto six adenine minus (ade-) plates. Four candidate revertants were obtained and they were restreaked onto ade- plates. The revertants were tested for other genetic markers by streaking on plates without uracyl (ura-), plates with no leucine (leu-), and minimal plates plus leucine. Growth was observed on ura- and minimal plus leu plates; no growth on leu- plates. Revertants were crossed with strain AB103.1 (Mat α, pep 4-3, leu 2-3, leu 2-112, ura 3-52, his 4-580) to determine if the reversion was due to extragenic suppression. Based on tetrad analysis, none of the four independent ade+ revertants were due to extragenic suppressor. Based on good growth and high spore viability, one of the revertants was selected and named PO17.

Expression and Purification of SODHA1 from Yeast

A 10 l culture of yeast strain PO17 transformed with pC1/1SODHA1 was grown to stationary phase in YEPD medium (Sherman, F., Fink, G. R., and Hicks, J. B., Methods of Yeast Genetics (1982), Cold Spring Harbor, N.Y.) containing 3 mM CuSO4 by inoculating the culture with 500 ml starter culture in minimal glucose medium lacking leucine.

One hundred seventy-three g of yeast cells expressing SODHA1 were lysed in 20 mM Tris-Cl, pH 8. After centrifugation, 900 ml of extract were obtained, the pH adjusted to 8.0 with NaOH, and stored at $-20°$ C. Eight hundred twenty ml were heated for 2 hr at 65° C., centrifuged, and the supernatant diluted with 8 vol 20 mM Tris-HCl, pH 8, to bring the conductivity down to 1 mmho. This was loaded onto a 400 ml column of DEAE Sepharose ® equilibrated with the same buffer. The column was washed extensively with 20 mM Tris-HCl, pH 8, and the SODHA1 eluted with 20 mM Tris-HCl, pH 8, 0.5M NaCl. The eluate was sterile filtered and stored at 4° C. Details of this purification are reported in Table 1 below.

TABLE 1

Purification of SODHA1

| | Volume (ml) | Protein (mg/ml) | Total Protein (g) | Units (ml) | Total Units | Specific Activity* (Units/g) | Fold Purification | Yield (%) |
|---|---|---|---|---|---|---|---|---|
| Extract | 820 | 13 | 10.7 | 10 | 8200 | 766 | 1.0 | 100 |
| Heated Extract | 720 | 6 | 4.3 | 11 | 7920 | 1842 | 2.25 | 97 |
| DEAE Eluate | 400 | 9 | 3.6 | 17 | 6800 | 1889 | 2.40 | 83 |

*Measured by pyrogallol method, Eur. J. Biochem (1974) 47:469–474.

As reported in Table 1, the yield was 83% overall, with a 2.4-fold purification. Since the SODHA1 is nearly pure, this indicates that it originally represented about 40% of the total protein found in the extract. Both the heating step and column gave good yields, 97% and 83%, respectively. The heating step was responsible for most of the purification (see FIGS. 4 and 5), but the column was valuable in removing nonproteinaceous contaminants such as lipid, carbohydrate, and nucleic acid.

An SDS gel (Coomassie Blue stain) of SODHA1 in various stages of purification is shown in FIG. 4. Again, it is immediately evident that most of the purification occurs during the heating step. The FIGURE also shows that there is a shift in mobility during the purification, resulting in a product that has 3 bands, the fastest migrating of which comigrates with the SODHA1 in the crude extract. This shift towards apparently higher molecular weight forms occurred both during the heating step and the ion-exchange chromatography. The cause of this alteration in the protein is unknown, but it does not seem to have very much effect on its function, since the SODHA1 has retained nearly all its activity after the purification. In fact, the purified SODHA1 has approximately the same specific activity as recombinant native hSOD using the pyrogallol assay.

Figure 5:
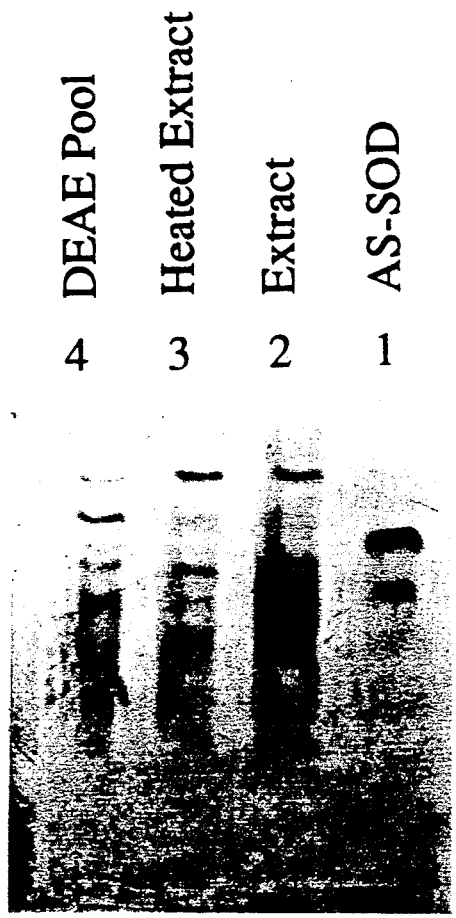
FIG. 5 is a photograph of an agarose gel analysis of the protein identified as SODHA1 in the examples, through its purification.

As a further test for alterations in SODHA1 during its purification, aliquots were subjected to agarose gel electrophoresis (FIG. 5). The procedure used Corning Universal 1% agarose gel equilibrated with 5 mM Tris, 30 mM EDTA. The gel was electrophoresed for 20 min at 250 V and stained with Amido Black. Reading from right to left, lane 1 is a control recombinant human SOD dimer (having two amino acid substitutions: $Cys_6$ to Ala and a $Cys_{111}$ to Ser), lane 2 contains crude extract, lane 3 heated extract, and lane 4 DEAE column eluate. Clearly, the SODHA1 actually exists as a mixture of species separable on this gel system. After heating, and after elution off the column, there are minor changes in the gel pattern. The identities of these species are unknown, but it appears that no major changes have occurred in the distribution of SODHA1 forms.

Characterization of the Purified SODHA1

Figure 6:
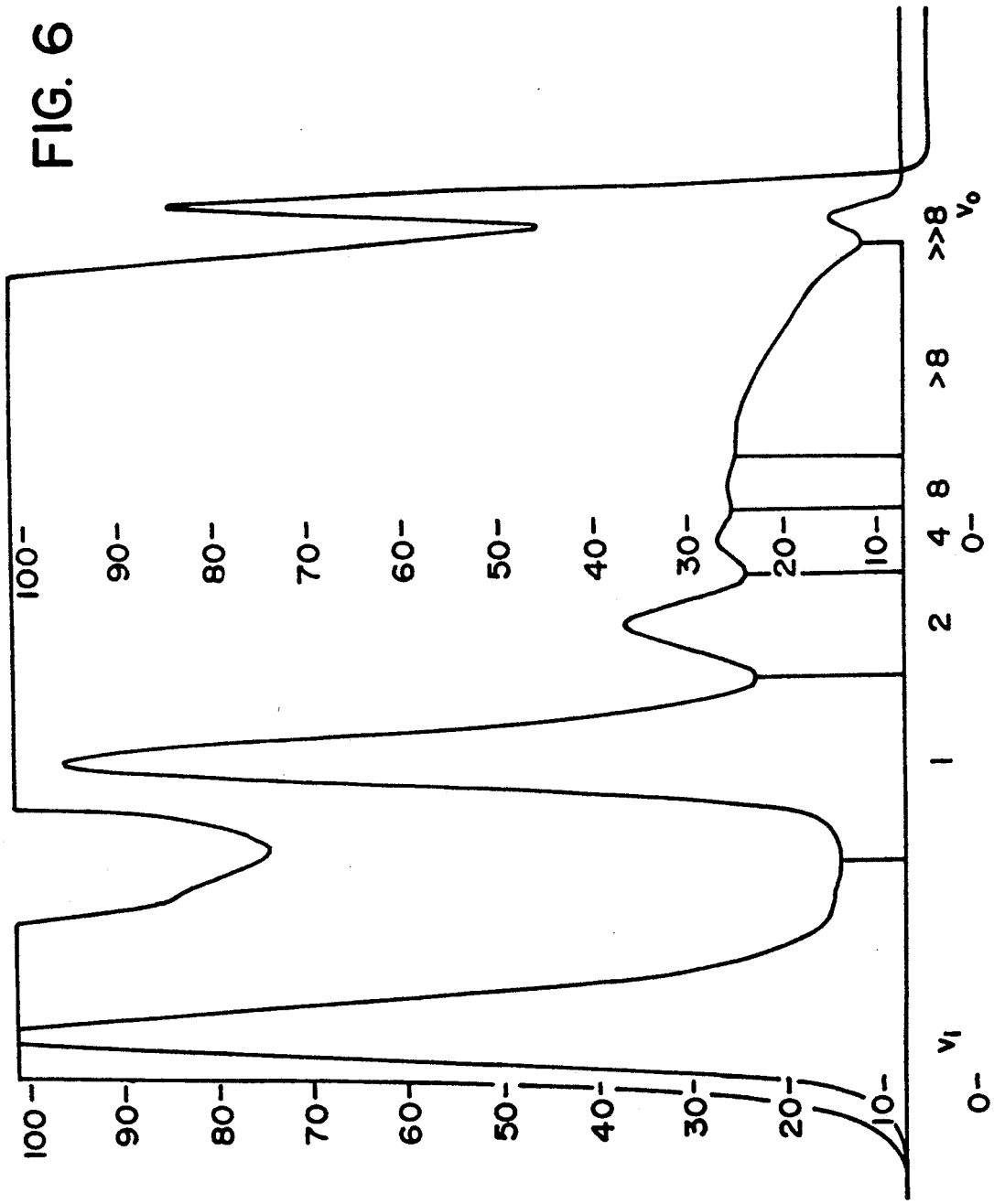
FIG. 6 is an absorbance tracing of eluate from a gel filtration of the purified protein identified as SODHA1 in the examples.

In addition to the experiments described above characterizing the purified SODHA1, the size distribution species was analyzed by gel filtration chromatography. Here, aliquots of crude extract and DEAE eluate were chromatographed on a calibrated AcA34 Ultragel® column (IBF Biotechnics). Yielding essentially identical results (the crude sample contained more UV-absorbing material in the void and included volumes; this was not, however, SODHA1). FIG. 6 shows the $OD_{280}$ absorbance tracing of material eluted off the column loaded with purified SODHA1. Two tracings are shown: The more sensitive one is 0.2 absorbance 280 units full scale, the other 2.0 absorbance units. The void volume (Vo) and included volume (Vi) are marked. The peaks are labeled with the probable number of covalent dimers per molecule in that peak (see Table 2).

Except for some UV-absorbing contaminating material eluting in the included volume, the absorbance tracing directly reflects the presence of SODHA1 (as assayed by SDS gel electrophoresis). The size distribution is presented in Table 2 below, as well as an interpretation of the subunit structures of the species, e.g., the 32 kd peak is almost certainly a single molecule of SODHA1. The 75 kd is likely to be a dimer of SODHA1, and the 125 kd, a trimer or possibly a tetramer of SODHA1. If these assignments are correct, nearly half of the protein is present as SODHA1 of nearly the same size as native SOD dimer. One-sixth is approximately twice the size of native SOD dimer, one-twelfth is approximately three times its size, etc. In summary, about half of the total mass is at least approximately twice the size of native SOD dimer.

TABLE 2

| Size Distribution of SODHA1 Multimers | | |
|---|---|---|
| Apparent Molecular Weight (kd) | Apparent Number of Units per Molecule | % of Total |
| 32 | 1 | 46.4 |
| 85 | 2 | 16.9 |
| 155 | 3 or 4 | 8.2 |
| 222 | 8 | 7.5 |
| 223-750 | >8 | 19.0 |
| 750 | >>8 | 2.0 |

Figure 7:
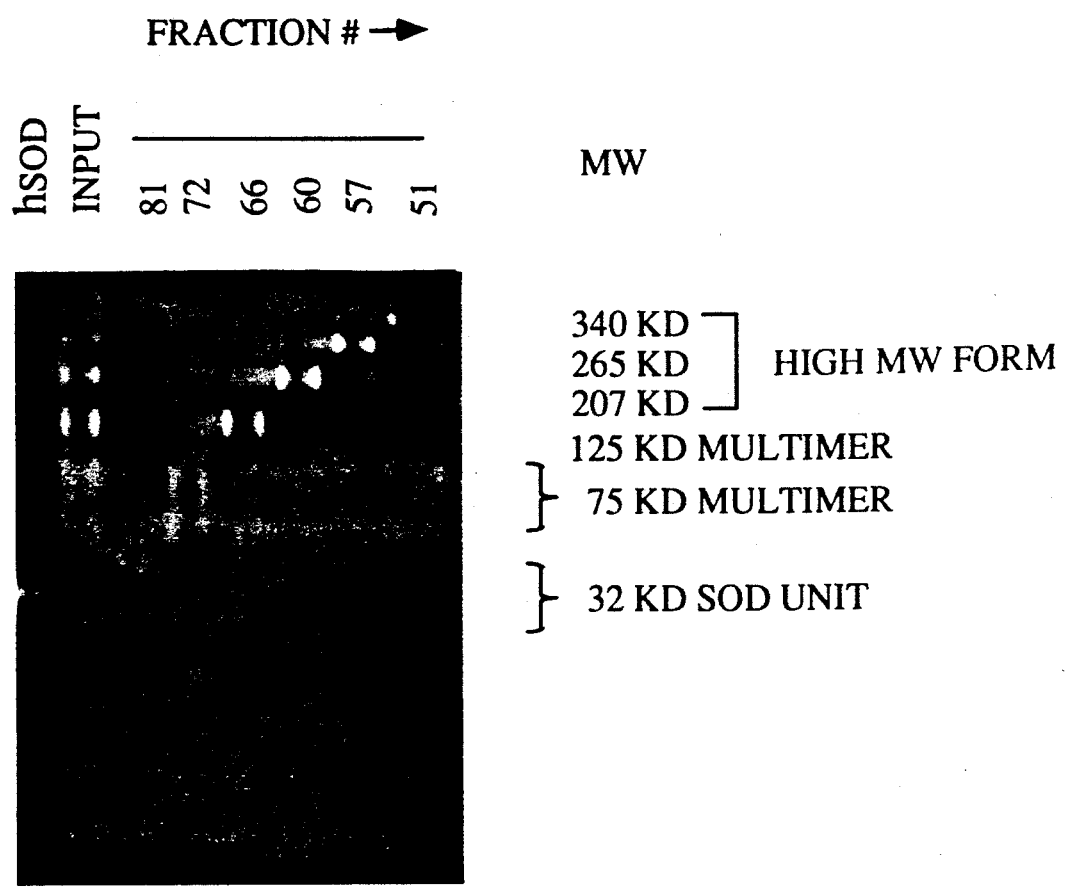
FIG. 7 is a photograph of an activity-stained PAGE analysis of the fractions from the gel filtration shown in FIG. 6.

Interestingly, all these species are active. When aliquots from the sizing column, loaded with crude extract here, were subjected to native polyacrylamide gel electrophoresis and stained for activity (hSOD was electrophoresed as a standard, and the column input is in the adjacent line). The results are shown in FIG. 7. All the species resolvable on the gel were seen to be active (fractions greater than 51 not shown here).

In conclusion, 3.6 g of SODHA1 has been purified by a combination of heating and ion-exchange chromatography. The SODHA1 exists as a population of active species, approximately half of which by mass is a monomeric form of SODHA1, with a distribution of various higher molecular weight species including some larger than 750 kd.

Stability of SODHA1 in Rat Plasma

Anesthetized rats (ca. 300 g in weight) were injected in the tail vein with 2,000 units (ca. 5 mg) of native hSOD, SODHA1, purified ca. 75 kd dimer, purified ca. 125 kd trimer, and higher molecular weight multimers (HMW-1). Serum samples (0.5 ml) were prepared from tail vein blood at 1, 5, 15, 30, 60, 120, 240 min and 24 hr. These samples were assayed for superoxide dismutase activity using the pyrogallol method. The results are shown in Table 3.

TABLE 3

| | Blood Plasma Retention of Multimeric Forms of SODHA1 in Rats (in SOD U/ml of plasma) | | | | | |
|---|---|---|---|---|---|---|
| Sample Time | Native Cu,Zn SOD | Monomer SODHA1 | Dimer SODHA1 | Trimer SODHA1 | HMW-1 SODHA1 | Total SODHA1 |
| 0' | 5.2 | 5.8 | 5.3 | 6.3 | 5.8 | 5.0 |
| 1' | 350 | 358 | 368 | 253 | 281 | 281 |
| 5' | 240 | 242 | 357 | 253 | 263 | 231 |
| 15' | 131 | 136 | 316 | 232 | 250 | 170 |
| 30' | 51 | 55 | 258 | 205 | 237 | 150 |
| 60' | 22 | 26 | 226 | 163 | 190 | 128 |
| 120' | 14 | 13 | 195 | 102 | 158 | 80 |
| 140' | 10 | 11 | 111 | 90 | 118 | 60 |
| 24 h | 8 | — | — | — | 38 | 20 |

These data indicate that native hSOD and the monomeric form of SODHA1 are both very rapidly removed from plasma with a half-life of approximately 7 min (taking 1 min as the 100% value). In contrast, the larger forms of hSOD (SODHA1 dimer, trimer, HMW-1, and total SODHA1) with molecular weights of greater than 75,000 have much longer half-lives on the order of 60-120 min.

Modifications of the above-described modes for carrying out the invention that are obvious to those of skill in the fields of biochemistry, genetic engineering, pharmacology, and related fields are intended to be within the scope of the following claims.

We claim:

1. A Cu/Zn superoxide dismutase (SOD) multimer comprising SOD units of two SOD monomers covalently coupled, carboxy terminus to amino terminus, to each other by a polypeptide spacer having 3-1000 amino acids, said spacer being substantially nonimmunogenic, and substantially insensitive to proteases.

2. The multimer of claim 1 wherein the SOD is human SOD (hSOD).

3. The multimer of claim 2 wherein the multimer contains 2 to 10 hSOD units.

4. The multimer of claim 2 wherein the multimer contains 2 to 4 hSOD units.

5. The multimer of claim 2 wherein the multimer contains 2 hSOD units.

6. The multimer of claim 1 wherein the spacer lacks cysteine residues and is substantially nonhydrophobic.

7. The multimer of claim 1 wherein the amino acid sequence of the spacer is substantially homologous to a connector domain or a fragment thereof, of a native endogenous protein which connector domain links functional domains of the endogenous protein in a manner that allows the functional domains to assume an appropriate tertiary structure and function independently.

8. The multimer of claim 7 wherein the connector domain is a hinge region of an immunoglobulin.

9. The multimer of claim 8 wherein the spacer has the amino acid sequence ProValProSerThrProProThrProSerProSerThrProProThrProSer.

10. A Cu/Zn superoxide dismutase (SOD) multimer comprising SOD units of two SOD monomers covalently coupled, carboxy terminus to amino terminus, to each other by a polypeptide spacer of 10 to 100 amino acids, said spacer being substantially nonimmunogenic, and substantially insensitive to protease.

11. The Cu/Zn SOD multimer of claim 10 wherein the polypeptide spacer is a hinge region of an immunoglobulin.

12. A multimer of Cu/Zn superoxide dismutase of the formula $$(\text{SOD monomer-IgA-SOD monomer})_x$$

wherein SOD monomer represents a Cu/Zn superoxide dismutase monomer, IgA represents a 10 to 100 amino acid long segment of an immunoglobulin hinge region, and x is an integer in the range of 2 and 4, inclusive.

13. A pharmaceutical composition for parenteral administration comprising the multimer of claim 1 admixed with a pharmaceutically acceptable vehicle that renders the composition injectable.

14. A method of increasing the circulatory life of Cu/Zn superoxide dismutase (SOD) comprising forming multimers composed of SOD units of two SOD monomers covalently coupled, carboxy terminus to amino terminus, to each other via a polypeptide spacer having 3-1000 amino acids, said spacer being substantially nonimmunogenic, and substantially insensitive to proteases.

15. A method for treating an individual for a medical condition that is alleviated by the reduction of superoxide molecules comprising administering a therapeutically effective amount of the multimer of claim 1 to the individual parenterally.

16. A composition of matter comprising two Cu/Zn superoxide dismutase (SOD) monomers covalently coupled, carboxy terminus to amino terminus, to each other, by a polypeptide spacer having 3 to 1000 amino acids, said spacer being substantially nonimmunogenic, and substantially insensitive to proteases.

17. DNA encoding a Cu/Zn superoxide dismutase (SOD) unit of two SOD monomers covalently coupled, carboxy terminus to amino terminus, to each other by a polypeptide spacer having 3 to 1000 amino acids, said spacer being substantially nonimmunogenic, and substantially insensitive to proteases.

18. An expression vector for expressing the DNA of claim 17 in an organism comprising the DNA of claim 18 operably connected to DNA that enables the expression of the DNA in the organism.

19. A host organism containing the vector of claim 18 which permits the expression of the DNA encoding the SOD unit.

20. A method for producing Cu/Zn superoxide dismutase (SOD) units, and multimers of said SOD units, said SOD units consisting essentially of two SOD monomers covalently coupled, carboxy terminus to amino terminus, to each other by a polypeptide spacer having 3–1000 amino acids, said spacer being substantially nonimmunogenic, and substantially insensitive to proteases, comprising growing the organism of claim 19 in a suitable growth medium under conditions that result in the expression of the DNA encoding the SOD unit.

* * * * *